United States Patent [19]

Hamer et al.

[11] Patent Number: 5,037,638

[45] Date of Patent: Aug. 6, 1991

[54] FLUORIDE RELEASE AGENT COPOLYMER PREPARED USING MORPHOLINOETHYL METHACRYLATE HYDROFLUORIDE COMONOMER

[75] Inventors: Martin Hamer, Skokie; Byoung I. Suh, Oak Brook, both of Ill.

[73] Assignee: Bisco Inc., Downers Grove, Ill.

[21] Appl. No.: 390,418

[22] Filed: Aug. 7, 1989

[51] Int. Cl.$^5$ .......................... A61K 7/18; A61K 31/78
[52] U.S. Cl. ........................................ 424/52; 424/81; 523/116
[58] Field of Search .................. 544/171; 424/81, 52, 424/171; 523/116

[56] References Cited

U.S. PATENT DOCUMENTS

| 2,806,838 | 9/1957 | Melamed | 544/171 |
| 2,824,861 | 2/1956 | Conbere et al. | 544/171 |
| 4,515,910 | 5/1985 | Rawls et al. | 523/116 |
| 4,657,941 | 4/1987 | Blackwell et al. | 523/116 |

FOREIGN PATENT DOCUMENTS 647846 12/1950 United Kingdom ............... 544/171

*Primary Examiner*—Thurman K. Page
*Assistant Examiner*—Peter F. Kulkosky
*Attorney, Agent, or Firm*—Marshall, O'Toole, Gerstein, Murray & Bicknell

[57] ABSTRACT

Morpholinoethyl methacrylate hydrofluoride is used as a fluoride-releasing component in a dental composite including a copolymer or interpolymer of an acrylic or methacrylic monomer.

6 Claims, No Drawings

FLUORIDE RELEASE AGENT COPOLYMER PREPARED USING MORPHOLINOETHYL METHACRYLATE HYDROFLUORIDE COMONOMER

The invention relates to polymeric materials useful in dentistry as sealants, restoratives, and/or adhesives, which contain fluorine and which can release fluoride ion to the adjacent tooth material, and to a method of using such materials to inhibit caries.

BACKGROUND OF THE INVENTION

It is known that certain fluoride-containing materials, which can be incorporated in resins used in dentistry as sealants, restoratives, and/or adhesives and also in devices such as denture reliners, orthodontic retainers, splint material, and finishing positioners, release fluoride ions at a rate sufficient to protect the adjacent tooth structure against caries. Specifically, Henry R. Rawls et al. have disclosed (U.S. Pat. Nos. 4,515,910 and 4,572,920) certain anion-exchange-site bearing monomers carrying fluoride ions which can be used to form interpolymers with other polymerizable monomers and which when used as dental materials slowly release fluoride ions at a rate sufficient to afford protection against caries.

In the aforementioned patents, the disclosures of which are incorporated herein by reference, the fluoride-containing materials are defined as polymerizable monomers containing an anion exchange site capable of carrying a fluoride ion, exemplified by certain alkylaminoalkyl acrylates or methacrylates. Specific examples of the fluoride-containing monomers taught by Rawls et al. are t-butylaminoethyl methacrylate hydrogen fluoride (t-BAEMA.HF), and N,N,N-trimethylaminoethyl methacrylate fluoride, which can be polymerized with alkyl acrylates and methacrylates, such as methyl methacrylate, ethyl methacrylate, butyl methacrylate, capryl methacrylate, palmityl methacrylate, stearyl methacrylate, and the corresponding acrylate esters; bisphenol-A derivatives of acrylic and methacrylic acid, such as 2,2-bis[4-methacroyloxyphenyl]propane(Bis-MA), 2,2bis[4-(2-hydroxy-3-methacroyloxypropoxy)phenyl]-propane(Bis-GMA) 2,2-bis[4-(2-methacroyloxy-ethoxy)phenyl]propane(Bis-EMA), and 2,2-bis[4-(3-methacroyloxy-propoxy)-phenyl]-propane(Bis-PMA); dimethacrylate derivatives of 1,2-cyclohexanedicarboxylic acid(c-HaDMA), and 4-cyclohexene-1,2-dicarboxylic acid(c-HeDMA); and dimethacrylate monomers containing urethane groups such as UEDMA and TUDMA, the structures of which are shown in Rawls U.S. Pat No. 4,572,920. The Rawls patents also describe the use for cross-linking in the interpolymers, of acrylic monomers such as ethyleneglycol dimethacrylate(EGDMA), trimethanolpropane trimethacrylate(TMPTMA), triethyleneglycol dimethacrylate(TEGDMA), polyethyleneglycol dimethacrylate(poly-EGDMA), and diethyleneglycol dimethacrylate(DEGDMA).

The interpolymers disclosed in the Rawls patents can be used either alone or together with filler materials such as silica to form dental materials for sealing or filling teeth while providing protection against caries.

SUMMARY OF THE INVENTION

In accordance with the present invention, there is provided an improved interpolymeric material of the type disclosed by Rawls et al. in which the fluoride-bearing monomer is morpholinoethyl methacrylate hydrofluoride (MEM.HF) having the formula

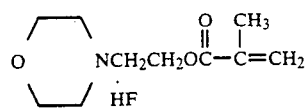

It has been found that MEM.HF provides unexpectedly superior properties when used as a source of fluoride ion in various dental restorative and protective materials such as those taught by Rawls et al. Specifically, fluoride-releasing dental materials formulated with MEM.HF as the source of fluoride ion are unexpectedly advantageous in producing cured resins which are harder than those produced with other fluoride-releasing components and maintain this hardening ability over a prolonged period of time. In addition, dental materials formulated with MEM.HF also release fluoride ions at a substantially higher rate.

DETAILED DESCRIPTION OF THE INVENTION

In accordance with the invention, it has been discovered that MEM.HF can be used in the same manner disclosed by the aforementioned Rawls patents for the production of interpolymeric resin materials which can be effectively deposited on dental surfaces and which deliver fluoride ions in sufficient quantity to inhibit caries without degradation of the deposited resin. In general, all of the acrylic monomers disclosed in the Rawls et al. patents can be used in the present invention, including alkyl acrylates and methacrylates, and particularly those wherein the alkyl groups contain up to 12 carbon atoms, high molecular weight acrylic materials such as those formed by reaction of bis-phenol A, cyclic dicarboxylic acids or urethanes with acrylic acids, and other acrylic monomers used for cross-linking, such as diethyleneglycol dimethacrylate.

The use of cross-linking monomers in the interpolymers of the invention is particularly desirable to produce a composition which is resistant to swelling, when filler is used in making restorative materials, or when a particularly strong adhesion is desired. Fillers which can be used together with the interpolymers of the invention include all of those known to the dental art for use in achieving high impact strength, resistance to moisture, and the like, including amorphous silica, glass, quartz, and other similar materials. Fillers can be incorporated to the extent of 50 to 80% by weight of the total composition.

The compositions of the invention can be used in accordance with the methods heretofore known for applying polymeric dental materials. For example, separate portions of a mixture of unreacted or partially reacted monomers, including MEM.HF, can be prepared, a first portion containing a polymerization initiator and a second portion containing an accelerator. The individual portions are mixed immediately prior to application on a dental surface. Polymerization is completed within an acceptable time limit, depending on the identity and concentration of the initiators and accelerators which are used. Suitable initiators include, without limitation, benzoyl peroxide, cumene hydroperoxide, and the like. Suitable accelerators which can be used in the present invention include, without limitation, N,N-dimethyl-p- toluidine, dihydroxyethyl-p-toluidine and other similar accelerators known to those skilled in the art.

The interpolymers of the present invention can also be prepared as polymerizable mixtures containing an accelerator and a photosensitizer, which are applied to a dental surface and caused to polymerize in situ by exposure to visible, ultraviolet, or other radiation, as is known by those skilled in the art.

In addition to using MEM.HF as a reactive monomer in a polymeric mixture which is polymerized in situ, the MEM.HF can be incorporated in a preformed solid polymer which is finely ground and used as a solid component, similar to a filler, in a dental restorative mixture.

The proportion of MEM.HF to be used in any particular mixture depends on the particular application, i.e., whether the restorative material is used as a sealer covering a relatively large area or as a dental restorative for filling cavities, as well as on the particular physical properties which are appropriate for the intended use. In general, however, about 1 to 40% of MEM.HF by weight, based on the copolymer or interpolymer, or 0.2 to 20% of MEM.HF by weight, based on the total composition of composites including a filler, can be used in materials used for dental restorative purposes.

The benefits of the invention are demonstrated by the following examples.

EXAMPLE 1

Preparation of MEM.HF

To a solution of morpholinoethyl methacrylate, 199.2 g (1.0 mole), in ethanol, 600 ml, was added 49% HF, 40.8 g (1.0 mole), with stirring and cooling at 15° C. in 20 minutes. Stirring was allowed to continue at the same temperature for an additional 1½ hours. A small sample was removed and evaporated and its infrared spectrum revealed complete conversion of the starting material to its hydrofluoride salt.

EXAMPLE 2

Light Cure Bonding Resins

Two fluoride-releasing light-cure bonding resins (A and B) having the composition set out in Table I were prepared. Each composition was divided in half. To one half of each of compositions A and B was added 3% by weight of t-BAEMA.HF, while to the other half of each composition was added 3% by weight of MEM.HF.

TABLE I

| Component[a] | A % (wt.) | B % (wt.) |
|---|---|---|
| Bis-GMA | 56 | 56 |
| TEGMA | 28 | 32.3 |
| TMPTMA | 4.4 | — |
| THFMA | 10 | 10.1 |
| Accelerator | 1 | 1 |
| Photosensitizer | 0.2 | 0.2 |
| UV Stabilizer | 0.4 | 0.4 |
| | 100.0 | 100.0 |

[a]BisGMA = 2,2bis[4-(2-hydroxy-3-methacryloxypropoxy)-phenyl] propane; TEGMA = triethyleneglycol dimethacrylate; TMPTMA = trimethylolpropane trimethacrylate; THFMA = tetrahydrofurfuryl methacrylate Each of compositions A and B was polymerized by illumination with a visible light source and the hardness of each of them (top and bottom surfaces) was measured, initially and after 21 and 43 days, using a commercially available (Barcol) hardness tester (Barber-Colman Impressor, model GYZJ 934-1). In general, Barcol hardness readings are obtained by placing a sample of the polymerizable mixture in a standard mold, exposing the sample to a standard light source for a standard time, e.g., 10 seconds or 20 seconds, and then measuring the hardness of the top and bottom surfaces of the sample.

The ability of the resins to release fluoride ions was determined by suspending the test sample in a measured volume of deionized water and measuring the fluoride content in solution by means of a commercially available meter (Orion Model SA 720) after 21 and 42 days. The results are summarized in Table II.

TABLE II

| Bonding Resin | Fluoride (3% by weight) | Barcol Hardness (10 sec. exposure to visible light) | | | Fluoride Release, μgF/cm² | |
|---|---|---|---|---|---|---|
| | | Initial | Days 21 | Days 43 | Days 21 | Days 42 |
| A | t-BAEMA.HF | 55/45* | 10/6 | 0/0 | 7.1 | 34.3 |
| | MEM.HF | 77/71 | 78/75 | 76/75 | 17.1 | 68.6 |
| B | t-BAEMA.HF | 0/0 | 0/0 | 0/0 | 12.9 | 34.3 |
| | MEM.HF | 72/72 | 76/76 | 78/78 | 35.7 | 70.0 |

*Top and bottom surfaces

The above results show that a cured bonding resin made with MEM.HF in accordance with the invention, releases fluoride ion at a substantially higher rate than one made with t-BAEMA.HF, and in addition, produces a cured resin which is also harder on exposure to visible light. The material produced with MEM.HF in accordance with the invention is accordingly particularly valuable as a fluoride-releasing component of a sealant or an adhesive composition in dental restorative materials.

EXAMPLE 3

A polymer was prepared in a bulk polymerization procedure using MEM.HF as one of the monomers, together with other monomers shown in Table III.

TABLE III

| Bulk Polymerization with MEM.HF | | |
|---|---|---|
| Reactant (in Order Added) | % (wt.) | g |
| Bis-GMA[1] | 30.0 | 7.50 |
| HEMA[2] | 30.0 | 7.50 |
| Tri-EDMA[3] | 10.0 | 2.50 |
| MEM.HF[4] | 29.8 | 7.45 |
| ABIN[5] | 0.2 | 0.05 |
| | 100.0% | 25.00 g |

[1]2,2-Bis[4-(2-hydroxy-3-methacryloyloxypropoxy)phenyl] propane
[2]2-hydroxyethyl methacrylate
[3]triethyleneglycol dimethacrylate
[4]morpholinoethyl methacrylate hydrofluoride; added as a 30% alcohol solution containing this amount
[5]azobis(isobutyronitrile)

Polymerization was carried out by heating at 75° to 85° C. for one hour.

The cured polymer, after being pulverized by freezing and grinding, was incorporated in a light-cure orthodontic paste containing strontium glass (62% by weight), finely divided silica (13% by weight), the polymer powder described in Table III (10% by weight), and a resin C (15% by weight) having the following composition:

| Resin C | |
|---|---|
| Ingredient | % by Weight |
| BisGMA | 39 |
| Urethane dimethacrylate (UDMA) | 31 |
| Triethylglycol dimethacrylate (TEDMA) | 27 |
| Amine derivative (accelerator) | 2 |
| Camphoroquinone (Photosensitizer) | 0.1 |
| Substituted benzophenone (UV Stabilizer) | 0.9 |

The orthodontic paste was light-cured for 10 seconds for the Barcol hardness test and 40 seconds each side for diametral tensile strength determination. The results showed diametral tensile strength of 35MN/m$^2$ and a Barcol hardness (10 seconds) of 89/87 (top/bottom).

The foregoing detailed description has been given for clearness of understanding only, and no unnecessary limitations should be understood therefrom, as modifications will be obvious to those skilled in the art.

We claim:

1. In a controlled fluoride-releasing dental composite comprising a copolymer of an acrylic or methacrylic monomer and a hydrogen fluoride salt of an aminomethacrylate, the improvement wherein said salt is morpholinoethyl methacrylate hydrofluoride said morpholine monomer salt providing an improved rate of fluoride release in comparison with the same dental composite copolymer system having t-butyl amino ethylmethacrylate fluoride in place of the morpholino monomer salt.

2. A composite in accordance with claim 1 wherein said morpholinoethyl methacrylate hydrofluoride is present in an amount sufficient to provide a caries-inhibiting amount of fluoride.

3. A composite in accordance with claim 2 wherein said morpholinoethyl methacrylate hydrofluoride is present in an amount of 1% to 40% by weight of said copolymer or interpolymer.

4. A composite in accordance with claim 1 further comprising about 50% to 90% by weight, based on the total composition, of a finely divided filler.

5. A composite in accordance with claim 4 comprising about 0.2% to 20% by weight of methacrylate hydrofluoride, based on the total composition.

6. A method for inhibiting caries in a tooth which comprises applying to the surface of said tooth an effective amount of a composition in accordance with claim 1.

* * * * *